United States Patent
Lee et al.

(10) Patent No.: US 11,897,841 B2
(45) Date of Patent: *Feb. 13, 2024

(54) ISOMERIZATION METHOD OF CYCLOHEXANE DICARBOXYLIC ACID

(71) Applicant: Hanwha Solutions Corporation, Seoul (KR)

(72) Inventors: Jong Kwon Lee, Daejeon (KR); Eun Jeong Kim, Daejeon (KR); Sun Uk Lee, Gunpo-si (KR); Nam Jin Jang, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 606 days.

This patent is subject to a terminal disclaimer.

(21) Appl. No.: 15/734,621

(22) PCT Filed: May 21, 2019

(86) PCT No.: PCT/KR2019/006088
§ 371 (c)(1),
(2) Date: Dec. 3, 2020

(87) PCT Pub. No.: WO2019/240393
PCT Pub. Date: Dec. 19, 2019

(65) Prior Publication Data
US 2021/0155572 A1    May 27, 2021

(30) Foreign Application Priority Data
Jun. 15, 2018  (KR) .................. 10-2018-0069246

(51) Int. Cl.
*C07C 51/353* (2006.01)
*B01J 21/06* (2006.01)

(52) U.S. Cl.
CPC ........... *C07C 51/353* (2013.01); *B01J 21/063* (2013.01); *B01J 21/066* (2013.01); *C07B 2200/09* (2013.01)

(58) Field of Classification Search
CPC ... B01J 21/063; B01J 21/066; C07B 2200/09; C07C 2601/14; C07C 51/353; C07C 61/09; A24F 40/10; A24F 40/40; A24F 40/46; A24F 7/04; B05B 17/0607; B06B 1/20

See application file for complete search history.

(56) References Cited

U.S. PATENT DOCUMENTS

| 5,231,218 A | 7/1993 | Summer |
| 2013/0072716 A1 | 3/2013 | Norman et al. |

FOREIGN PATENT DOCUMENTS

| CN | 1608042 | 4/2005 |
| CN | 1935773 | 3/2007 |
| CN | 105582926 | 5/2016 |
| CN | 105582927 | 5/2016 |
| CN | 112334439 | 6/2023 |
| EP | 1449822 | 8/2004 |
| JP | 49081349 | 8/1974 |
| JP | 49082648 | 8/1974 |
| JP | 58024540 | 2/1983 |
| JP | 3549885 | 3/1996 |
| JP | H08502747 | 3/1996 |
| JP | 2000-191602 | 7/2000 |
| JP | 3807135 | 7/2000 |
| JP | 2000191602 | * 7/2000 |
| JP | 2000-319204 | 11/2000 |
| JP | 39027244 | 2/2001 |
| JP | 2001-151716 | 6/2001 |
| JP | 2002-363126 | 12/2002 |
| JP | 2003-128620 | 5/2003 |
| JP | 2008-063311 | 3/2008 |
| JP | 2010-163439 | 7/2010 |
| JP | 2010-270093 | 12/2010 |
| JP | 2017-178808 | 10/2017 |
| JP | 2018-076282 | 5/2018 |
| KR | 10-2005-0100941 | 10/2005 |
| KR | 20050100941 | * 10/2005 |

OTHER PUBLICATIONS

JP2000191602 translated (Year: 2000).*
KR20050100941 translated (Year: 2005).*
KIPO, PCT Search Report & Written Opinion of PCT/KR2019/006088 dated Aug. 27, 2019.
EPO, Search Report of EP 19818926.8 dated Feb. 3, 2022.

* cited by examiner

*Primary Examiner* — Yevgeny Valenrod
*Assistant Examiner* — Blaine G Doletski
(74) *Attorney, Agent, or Firm* — LEX IP MEISTER, PLLC

(57) ABSTRACT

Provided is an isomerization method of cyclohexane dicarboxylic acid using zirconia or titania as an isomerization catalyst.

7 Claims, 5 Drawing Sheets

[FIG. 1]
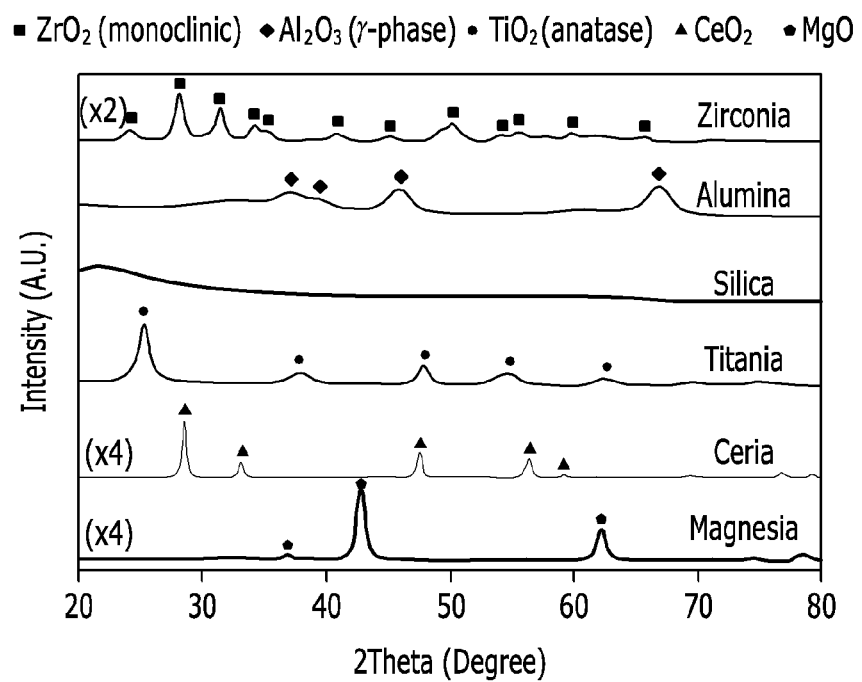

[FIG. 2]
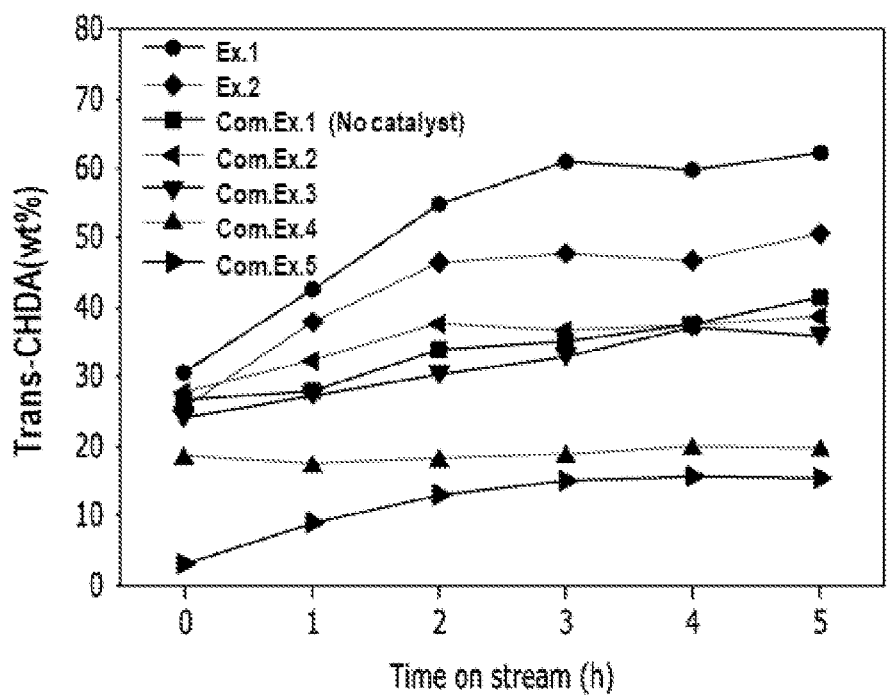

[FIG. 3]
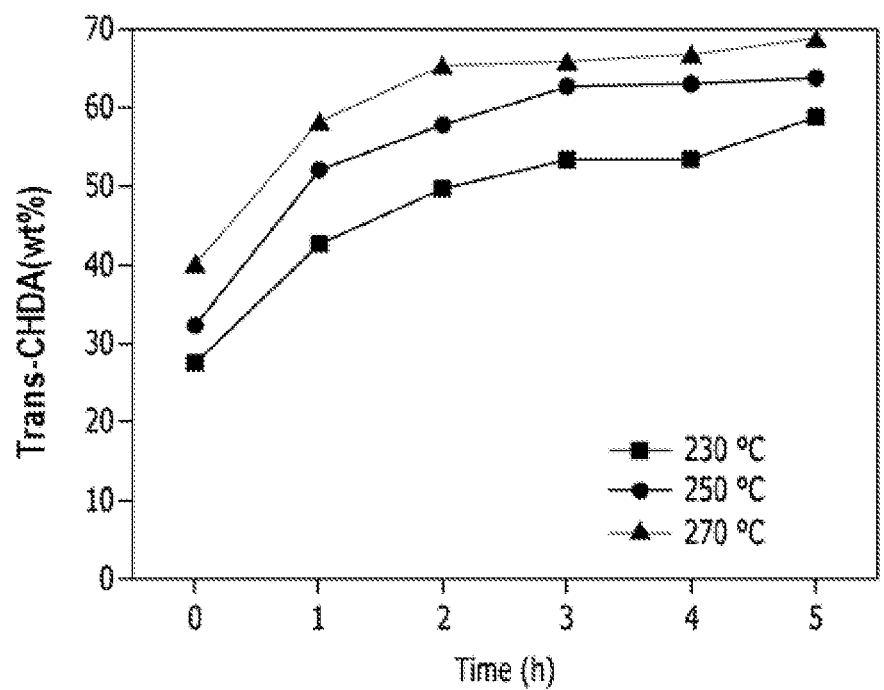

[FIG. 4]
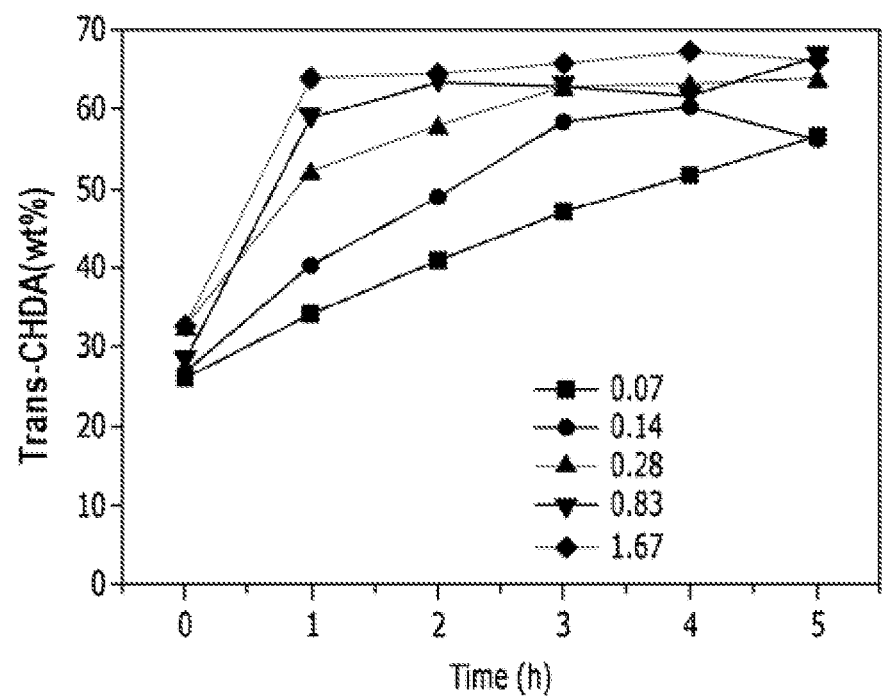

[FIG. 5]
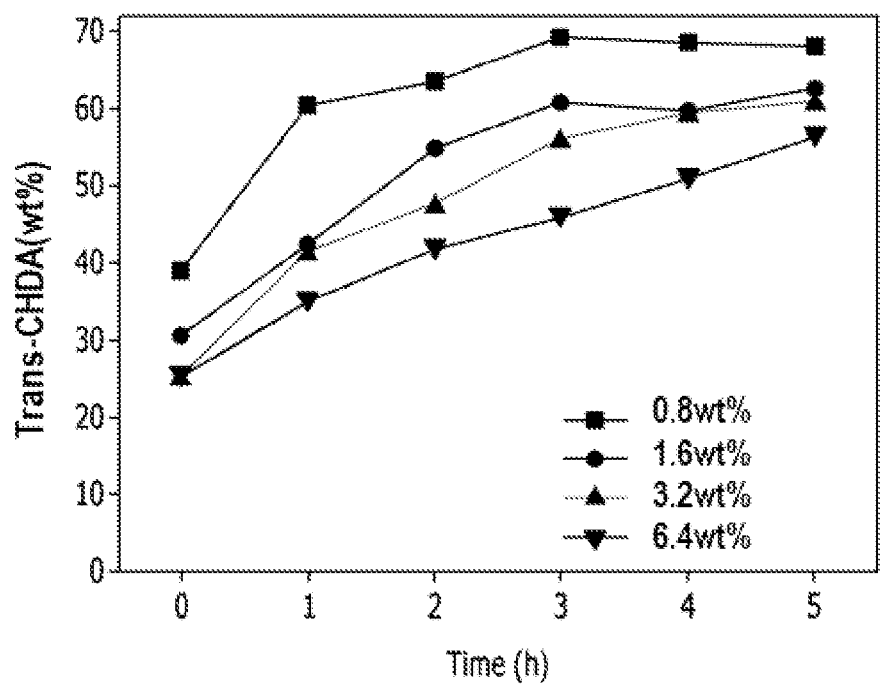

ISOMERIZATION METHOD OF CYCLOHEXANE DICARBOXYLIC ACID

CROSS-REFERENCE TO RELATED APPLICATION(S)

The present application is based on, and claims priority from, Korean Patent Application No. 10-2018-0069246, filed on Jun. 15, 2018, the disclosure of which is hereby incorporated by reference herein in its entirety.

TECHNICAL FIELD

The present invention relates to an isomerization method of cyclohexane dicarboxylic acid (CHDA), and more particularly, a method of preparing trans-cyclohexane dicarboxylic acid (t-CHDA) from cis-cyclohexane dicarboxylic acid (c-CHDA) through a catalytic isomerization method.

BACKGROUND ART

Cyclohexane dicarboxylic acid (CHDA) is widely used as a raw material for medicines, synthetic resins, synthetic fibers, dyes, etc. In particular, trans-cyclohexane dicarboxylic acid (t-CHDA) is used as a raw material in producing resins and fibers required to have heat resistance, weather resistance, and strength properties. Therefore, there is a need for CHDA having a high concentration of t-CHDA.

In general, CHDA is prepared by hydrogenating terephthalic acid (TPA) or hydrogenating a benzene ring of a TPA derivative. For example, with regard to the method of hydrogenating a benzene ring of a TPA derivative, there is a method of hydrogenating the benzene ring (nuclear hydrogenation) after converting a carboxyl group of TPA to a metal salt such as a sodium salt or various esters, or a method of nuclear hydrogenating the carboxyl group.

However, in these methods, isomers are generated by hydrogenation of the TPA benzene ring, and the resulting CHDA is in the form of a mixture of c-CHDA and t-CHDA. The concentration of t-CHDA in the obtained CHDA is as low as less than 50%, although it depends on the reaction conditions.

Accordingly, various methods have been studied in order to increase the concentration of t-CHDA in CHDA, and among them, the most studied method is a thermal isomerization method.

The thermal isomerization method includes a method of performing thermal isomerization of CHDA, a method of performing thermal isomerization of an aqueous solution of CHDA, and a method of performing thermal isomerization using an alkali salt. Specifically, the method of performing thermal isomerization of CHDA is a method of isomerizing c-CHDA to t-CHDA by heating c-CHDA above the melting point of t-CHDA (see Patent Documents 1 and 2). However, in this method, since heating is performed at a temperature above the melting point of the t-isomer, the obtained t-CHDA is very hard and difficult to handle. Moreover, there is a problem in that t-CHDA having a high purity of 98% may be finally obtained only when t-CHDA is heat-treated and then recrystallized from water using activated carbon. To solve this problem, a method of obtaining t-CHDA after mixing the isomerized t-CHDA with an inert liquid substance to prepare a suspension has been suggested. However, it is necessary to increase the temperature of the reaction system above the melting point, and to disperse the melt together with liquid paraffin. There is also a problem in that a process of removing liquid paraffin from the dispersed t-CHDA is required, and it is difficult to completely remove paraffin.

In addition, in the case of the method of performing thermal isomerization of an aqueous solution of CHDA (see Patent Document 3), in which t-CHDA is obtained by heating the aqueous solution of c-CHDA to 240° C. or higher under a pressure, an isomerization proportion to t-CHDA is not high.

Another method of performing thermal isomerization using an alkali salt (see Patent Document 4), in which an alkali metal salt or alkaline earth metal salt of a c/t-CHDA mixture is heated at a solid phase in the presence of an alkali metal hydroxide or alkaline earth metal hydroxide to prepare t-CHDA, has a problem in that impurities of the alkali metal or the alkaline earth metal are generated because the reaction product is dissolved after completion of the reaction and converted into a carboxylic acid through a precipitation reaction with an acid.

Accordingly, there is a need to develop a novel method capable of efficiently isomerizing c-CHDA to t-CHDA without concern about the above problems.

(Patent Document 1) Patent Document 1: JP-B-39-027244

(Patent Document 2) Patent Document 2: JP-A-49-081349

(Patent Document 3) Patent Document 3: JP-A-49-082648

(Patent Document 4) Patent Document 4: JP-A-58-024540

DETAILED DESCRIPTION OF THE INVENTION

Technical Problem

To solve the above problems of the prior art, there is provided an isomerization method of CHDA, the method capable of efficiently preparing CHDA having a high content of t-CHDA from CHDA mainly including c-CHDA.

Technical Solution

To achieve the above object, according to one embodiment of the present invention, there is provided an isomerization method of cyclohexane dicarboxylic acid, the method including the step of isomerizing a cis isomer to a trans isomer by heat-treating a mixed solution which is prepared by mixing CHDA including the cis isomer, water, and an isomerization catalyst, wherein the mixed solution includes the cyclohexane dicarboxylic acid in an amount of 0.5% by weight to 30% by weight with respect to the total weight of the mixed solution, and the isomerization catalyst includes one or more of oxide of a transition metal of Group 4, and is added in an amount such that a weight ratio of the isomerization catalyst to the cyclohexane dicarboxylic acid (a weight ratio of isomerization catalyst/cyclohexane dicarboxylic acid) of 0.1 or more.

Advantageous Effects

A trans/cis ratio in CHDA may be easily controlled according to an isomerization method of CHDA according to the present invention. Accordingly, CHDA rich in the trans isomer may be prepared from CHDA rich in the cis isomer.

BRIEF DESCRIPTION OF THE DRAWINGS

FIG. 1 shows a graph showing the results of X-ray diffraction analysis of isomerization catalysts used in Examples 1 and 2, and Comparative Examples 2 to 4 according to Experimental Example 1;

FIG. 2 shows a graph showing the results of evaluating effects of the catalysts on the isomerization reaction of CHDA according to Experimental Example 2;

FIG. 3 shows a graph showing the results of evaluating effects of the reaction temperature on the isomerization reaction of CHDA according to Experimental Example 3;

FIG. 4 shows a graph showing the results of evaluating effects of weight ratios of isomerization catalyst/CHDA on the isomerization reaction of CHDA according to Experimental Example 4; and FIG. 5 shows a graph showing the results of evaluating effects of CHDA concentrations on the isomerization reaction of CHDA according to Experimental Example 5.

DETAILED DESCRIPTION OF THE EMBODIMENTS

The terms used in this description are just for explaining exemplary embodiments and it is not intended to restrict the present invention. The singular expression may include the plural expression unless it is differently expressed contextually. It must be understood that the term "include", "equip", or "have" in the present description is only used for designating the existence of characteristics taken effect, steps, components, or combinations thereof, and do not exclude the existence or the possibility of addition of one or more different characteristics, steps, components or combinations thereof beforehand.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, an isomerization method of CHDA and an isomerization catalyst according to specific embodiments of the present invention will be described in more detail.

An isomerization method of CHDA according to one specific embodiment of the present invention includes the step of isomerizing a cis isomer to a trans isomer by heat-treating a mixed solution which is prepared by mixing CHDA including the cis isomer, water, and an isomerization catalyst.

In the isomerization method, the isomerization catalyst is an oxide containing a transition metal of Group 4, such as zirconium (Zr), titanium (Ti), or hafnium (Hf).

In the isomerization reaction, the isomerization reaction to t-CHDA proceeds through a reaction mechanism in which c-CHDA is adsorbed onto the isomerization catalyst, the isomerization occurs, and the product is desorbed. At this time, the interaction between c-CHDA and the isomerization catalyst, the adsorption of the reactant onto the isomerization catalyst, and the desorption of the product from the isomerization catalyst after completion of the reaction greatly influence the isomerization reaction efficiency and the yield of the isomerization product. Accordingly, the isomerization catalyst must exhibit appropriate adsorption and desorption strength for both the reactant and the product, respectively. The oxide of the transition metal of Group 4 used as the isomerization catalyst in the present invention exhibits excellent interaction with c-CHDA, as compared with inorganic oxides such as silica and ceria, and thus it may exhibit excellent reaction efficiency during the isomerization reaction of CHDA. In addition, unlike transition metal oxides such as alumina and magnesia, it exhibits appropriate adsorption and desorption strength for the reactant and the product during isomerization, respectively. Therefore, there is no concern about the yield reduction which is attributed to that the product t-CHDA may be strongly adsorbed onto the isomerization catalyst and thus may not be separated therefrom even after completion of the isomerization reaction. In addition, when the isomerization catalyst is surface-treated or modified to have a functional group as in the prior art, it may influence the adsorption with respect to the reactant and desorption with respect to the product, and as a result, the isomerization reaction efficiency may decrease or the yield may decrease. Since the isomerization catalyst of the present invention may not be surface-treated or modified, it may exhibit appropriate adsorption and desorption strength.

Specific examples of the isomerization catalyst applicable in the present invention may include zirconia or titania, and any one thereof or a mixture of two or more thereof may be used.

The zirconia has a high melting point to exhibit excellent fire resistance, and is chemically very stable. Accordingly, there is no concern about side reactions occurring during the isomerization reaction. In addition, since zirconia exhibits a sufficient interaction with the reactant, it may exhibit more excellent catalytic effects on the CHDA isomerization reaction. The zirconia may have a variety of crystal structures of monoclinic, tetragonal, and cubic forms. Among them, it may be more preferable that the zirconia has the crystal structure of the monoclinic form, in terms of thermal/chemical stability and the catalytic effect on the CHDA isomerization reaction.

The titania has excellent chemical and physical stability, and exhibits a sufficient interaction with the reactant, thereby exhibiting more excellent catalytic effects during the CHDA isomerization reaction. The titania may have a crystal structure of anatase, rutile, or brookite. Among them, it may be more preferable that the titania has the crystal structure of the anatase, in terms of the ease of catalyst preparation and the catalytic effect on the CHDA isomerization reaction.

According to the isomerization method of CHDA according to one specific embodiment of the present invention, the amount of the isomerization catalyst may be appropriately controlled according to the content of CHDA including the cis isomer as the reactant. Specifically, as the content of the isomerization catalyst increases, relative to CHDA, the reaction rate increases. Therefore, in the isomerization method of CHDA according to one specific embodiment of the present invention, the isomerization catalyst may be added in an amount such that the weight ratio of isomerization catalyst/CHDA is 0.1 or more. However, when the content of the isomerization catalyst is at a predetermined level or more, relative to CHDA, the effect of increasing the reaction rate is not increased as much as the amount of use, and thus the reaction efficiency decreases. From this point of view, the isomerization catalyst may be more specifically added in an amount such that the weight ratio of isomerization catalyst/CHDA satisfies 0.1 to 2.0. When the weight ratio of isomerization catalyst/CHDA is less than 0.1, it is difficult to obtain the sufficient isomerization effect, and when the weight ratio of isomerization catalyst/CHDA is more than 2.0, the increase in the reaction efficiency may be insufficient, considering the amount of the catalyst, as described above. It is more preferable that the isomerization catalyst is added in an amount such that the weight ratio of isomerization catalyst/CHDA is 0.14 or more, or 0.25 or more, or 0.28 or more, or 0.5 or more, or 0.8 or more, and 1.8 or less, or 1.7 or less, or 1.67 or less, considering the effect of improving the reaction rate and the effect of increasing the yield of t-CHDA by the control of the weight ratio of isomerization catalyst/CHDA.

Meanwhile, in the isomerization method of CHDA using the above-described isomerization catalyst according to one specific embodiment of the present invention, a mixed solution which is prepared by mixing CHDA including the cis isomer, water, and the isomerization catalyst is used.

The CHDA may include only the cis isomer, or may further include the trans isomer, in addition to the cis isomer. When the CHDA further includes the trans isomer, its content may be preferably less than 50% by weight, and more specifically 40% by weight or less with respect to the total weight of CHDA, in order to obtain the sufficient isomerization effect.

The mixed solution is prepared by dissolving CHDA and the catalyst in water. At this time, in order to increase the solubility of CHDA, and furthermore, to increase the isomerization efficiency, an alkali metal, an alkaline earth metal, or a basic aqueous solution may be further added, or a stirring process may be optionally further performed.

In addition, the concentration of CHDA in the mixed solution influences the isomerization reaction of CHDA. Specifically, as the concentration of CHDA decreases, the reaction rate of the isomerization reaction increases. However, when the concentration of CHDA is too low, it is apprehended that the generation and yield of t-CHDA may decrease, and the reaction efficiency may decrease. If the concentration of CHDA is too high, the reaction rate may decrease, and thus it may be difficult to obtain the sufficient isomerization effect. Accordingly, in the isomerization method of CHDA according to one specific embodiment of the present invention, the concentration of CHDA may be 0.5% by weight to 30% by weight with respect to the total weight of the mixed solution. When the concentration of CHDA is less than 0.5% by weight, the production amount and yield of the product are too small, and the efficiency is low. On the contrary, when the concentration of CHDA exceeds 30% by weight, it is apprehended that the reaction rate becomes slow, the preparation process is prolonged, and the isomerization effect decreases. It is also apprehended that high concentration of CHDA may precipitate in a solid phase. More specifically, the concentration of CHDA in the mixed solution may be 0.8% by weight or more, 20% by weight or less, or 10% by weight or less, or 6.5% by weight or less. In terms of the effect of increasing the reaction rate and the effect of improving t-CHDA yield according to the control of the concentration of CHDA, the concentration of CHDA in the mixed solution may be 0.8% by weight or more, 5% by weight or less, or 3.5% by weight or less, or 2% by weight or less, or 1% by weight or less.

After the isomerization catalyst is added, the isomerization reaction occurs when the mixed solution is heat-treated by a method, such as heating. At this time, the reaction rate may be controlled by controlling the reaction temperature. Specifically, as the reaction temperature increases during the isomerization reaction, the reaction rate increases. When the reaction temperature exceeds a predetermined level, it may be difficult to control the reaction rate. Accordingly, in the isomerization method of CHDA according to one specific embodiment of the present invention, the isomerization catalyst is added, and then a process of heat-treating the reaction system in the temperature range of 220° C. to 280° C. is performed. In the isomerization reaction, when the temperature is lower than 220° C., the reaction rate is slow, and when the temperature is higher than 280° C., it may be difficult to control the reaction rate. In terms of the effect of increasing the reaction rate and the effect of improving the t-CHDA yield according to the control of the reaction temperature, the heat treatment process may be more preferably performed at a temperature of 230° C., or 250° C. or higher, and 270° C. or lower.

In addition, a stirring process may be performed during the isomerization reaction, and the reaction efficiency during the isomerization reaction may be improved by controlling the speed of the stirring process. Specifically, the stirring process may be performed at a speed of 500 rpm to 2000 rpm, and more specifically, it may be preferably performed at a speed of 700 rpm or more, 1300 rpm or less, or 1000 rpm or less.

Meanwhile, the stirring process may be performed using a common stirring device.

In terms of the process efficiency, it may be more preferable that the isomerization reaction is performed for 2 hr to 5 hr under conditions that satisfy all of the above isomerization reaction conditions.

As a result of the above reaction, c-CHDA in CHDA is converted to t-CHDA with excellent efficiency. Specifically, according to one specific embodiment of the present invention, the content of t-CHDA in the final prepared CHDA is 50% by weight or more, and more specifically, 60% by weight or more with respect to the total weight of CHDA.

Further, according to one specific embodiment of the present invention, when the above-described isomerization catalyst is used, it is possible to easily increase and control the content of the trans isomer in CHDA, and there is no concern about side reactions. Specifically, the content of organic impurities in the final prepared CHDA after the isomerization reaction is 1% by weight or less.

According to another embodiment of the present invention, provided is the isomerization catalyst useful for preparing t-CHDA.

The isomerization catalyst for preparing t-CHDA includes an oxide of a transition metal of Group 4, and specific details are the same as described above.

Hereinafter, the present invention will be described in more detail with reference to Examples. However, the following Examples are for illustrative purposes only, and the scope of the present invention is not intended to be limited by the following Examples. In addition, in the following Examples and Comparative Examples, "%" and "part" indicating the content are based on weight, unless otherwise mentioned.

Example 1

For isomerization reaction of CHDA, a batch reactor that is able to withstand 300° C. and 150 bar was selected as a reactor. To the prepared batch reactor, 4.05 g of CHDA containing a cis isomer, 1.125 g of zirconia (monoclinic), and 250 g of distilled water as a solvent were added, and the temperature of the mixed solution was raised to 250° C. under stirring at 50 rpm (CHDA concentration in the mixed solution: 1.6% by weight, a weight ratio of zirconia/CHDA=0.28). When the temperature of the mixed solution reached 250° C., the stirring speed was increased to 1000 rpm and the reaction was allowed for 5 hr under stirring.

Example 2

Reaction was performed in the same manner as in Example 1, except that titania (anatase) was used instead of zirconia in Example 1.

Comparative Example 1

4.05 g of CHDA was added and dissolved in 250 g of distilled water, and the mixture was reacted for 5 hr under stirring at 1000 rpm at 250° C. (CHDA concentration in the aqueous solution: 1.6% by weight).

Comparative Example 2

Reaction was performed in the same manner as in Example 1, except that ceria was used instead of zirconia in Example 1.

Comparative Example 3

Reaction was performed in the same manner as in Example 1, except that silica (amorphous) was used instead of zirconia in Example 1.

Comparative Example 4

Reaction was performed in the same manner as in Example 1, except that alumina (gamma-phase) was used instead of zirconia in Example 1.

Comparative Example 5

Reaction was performed in the same manner as in Example 1, except that magnesia was used instead of zirconia in Example 1.

Experimental Example 1: Analysis of Catalysts

X-ray diffraction analysis was performed to examine the crystal structures of the catalysts used in Examples 1 and 2 and Comparative Examples 2 to 5, and the results are shown in FIG. 1.

Experimental Example 2: Evaluation of Effects of Catalysts on Isomerization Reaction of CHDA In order to evaluate the effects of the catalysts on the isomerization reaction of CHDA, the t-CHDA contents were measured, after completing the isomerization reactions according to Examples 1 and 2 and Comparative Examples 1 to 5. The measured t-CHDA contents were converted in terms of the yield, and shown in FIG. 2.

As a result, in Examples 1 and 2, in which the isomerization catalyst according to the present invention was used, the t-CHDA content after completion of the final reaction was 50% by weight or more, indicating a remarkable increase, as compared with Comparative Example 1 (about 40% by weight), in which no isomerization catalyst was used. In particular, Example 1, in which zirconia was used, showed the t-CHDA content of about 60% by weight, which was higher than that of Example 2 (t-CHDA content of about 50% by weight), in which titania was used.

Meanwhile, in Comparative Examples 2 and 3, in which ceria and silica were used as the isomerization catalyst, respectively, the t-CHDA content was equivalent to that of Comparative Example 1 (about 40% by weight), in which no catalyst was used, indicating that ceria and silica have little catalytic effect on the CHDA isomerization reaction. In addition, Comparative Examples 4 and 5, in which alumina and magnesia were used as the isomerization catalyst, respectively, showed excellent catalytic effects on the isomerization reaction, but the yield was greatly reduced because the reactant adsorbed onto the catalyst was not desorbed (the yield of Examples 1 to 3: 99.9% by weight or more, the yield of Comparative Example 4: about 32% by weight, and the yield of Comparative Example 5: about 17% by weight).

These results confirmed that the isomerization catalysts used in the present invention exhibit the excellent effect on CHDA isomerization.

Experimental Example 3: Evaluation of Effects of Reaction Temperature on Isomerization Reaction of CHDA In order to evaluate the effect of the reaction temperature on the isomerization reaction of CHDA using the isomerization catalyst, the isomerization reaction was performed by varying the reaction temperature, and changes in the t-CHDA content were measured.

In detail, the isomerization reaction was performed in the same manner as in Example 1, except that the reaction temperature was changed to 230° C., 250° C., and 270° C., respectively (catalyst: zirconia (monoclinic)). The results are shown in FIG. 3.

As a result, as the reaction temperature increased, the reaction rate increased, leading to high content of t-CHDA. However, when the reaction temperature is low, the reaction rate becomes slow and processability is deteriorated, and when the reaction temperature is too high, it is difficult to control the reaction rate. From this point of view, it is preferable that the reaction temperature during the isomerization reaction is in the range of 230° C. to 270° C. in order to obtain sufficient t-CHDA isomerization effect for an appropriate reaction time.

Experimental Example 4: Evaluation of Effects of Content Ratio of Isomerization Catalyst/CHDA on Isomerization Reaction of CHDA In order to evaluate the effect of the content ratio of catalyst and CHDA on the isomerization reaction of CHDA, the isomerization reaction was performed by varying the weight ratio of isomerization catalyst/CHDA, and changes in the t-CHDA content were measured.

In detail, the isomerization reaction was performed in the same manner as in Example 1, except that the weight ratio of isomerization catalyst/CHDA was changed to 0.07, 0.14, 0.28, 0.83, and 1.67, respectively (catalyst: zirconia (monoclinic)). The results are shown in FIG. 4.

As a result, when the weight ratio of isomerization catalyst/CHDA was 0.07, the reaction rate was slow, and the isomerization effect was lower than that of the case where the weight ratio of catalyst/CHDA was 0.1 or more. However, as the weight ratio of catalyst/CHDA increases to 0.1 or more, the reaction rate increased, and high content and yield of t-CHDA were observed after completion of the reaction. In addition, from the result when the weight ratio of isomerization catalyst/CHDA was 1.67, it is expected that when the weight ratio is higher than 1.67 to exceed a predetermined level, specifically, when it exceeds 2.0, the effect of increasing the reaction rate is poor, considering the amount of use, and thus the reaction efficiency may decrease.

Experimental Example 5: Evaluation of Effects of CHDA Concentration on Isomerization Reaction of CHDA In order to evaluate the effect of the CHDA concentration on the isomerization reaction of CHDA, the isomerization reaction was performed by varying the CHDA concentration, and changes in the t-CHDA content were examined until the reaction was completed.

In detail, the isomerization reaction was performed in the same manner as in Example 1, except that the CHDA concentration was changed to 0.8% by weight, 1.6% by weight, 3.2% by weight and 6.4% by weight, respectively (catalyst: zirconia (monoclinic)). The results are shown in FIG. 5.

As a result, as the CHDA concentration was lower, the reaction rate was higher, and the t-CHDA content was also high after completion of the reaction. In addition, when the concentration of the reactant and the ratio of the catalyst used are equal, even though the CHDA concentration in the mixed solution is increased to 30% by weight, the reaction rate and the t-CHDA content are expected to be similar or equal to that of the CHDA concentration of 6.4% by weight. However, when the CHDA concentration is more than 30% by weight, it is apprehended that CHDA may precipitate in a solid phase. Therefore, the CHDA concentration in the mixed solution is preferably 30% by weight or less. In particular, when the use of the isomerization catalyst and the reaction temperature conditions are considered at the same time, the CHDA concentration of 3.2% by weight or less is more preferred.

The above experimental results indicate that the t-CHDA content may be increased and controlled through the isomerization reaction using the isomerization catalyst containing an oxide of a transition metal of Group 4, such as zirconia or titania, and the isomerization efficiency of t-CHDA may be further improved by controlling the CHDA concentration, the amount of the catalyst, and the reaction temperature during the isomerization reaction.

The invention claimed is:

1. An isomerization method of cyclohexane dicarboxylic acid, comprising the step of isomerizing a cis isomer to a trans isomer by heat-treating a mixed solution which is prepared by mixing cyclohexane dicarboxylic acid comprising the cis isomer, water, and an isomerization catalyst,
    wherein the mixed solution comprises the cyclohexane dicarboxylic acid in an amount of 0.5% by weight to 30% by weight with respect to the total weight of the mixed solution, and
    the isomerization catalyst comprises one or more of oxide of a transition metal of Group 4, and is added in an amount such that a weight ratio of the isomerization catalyst to the cyclohexane dicarboxylic acid (a weight ratio of isomerization catalyst/cyclohexane dicarboxylic acid) of 0.1 or more.

2. The isomerization method of cyclohexane dicarboxylic acid of claim 1, wherein the oxide of the transition metal of Group 4 comprises one or more selected from the group consisting of zirconia and titania.

3. The isomerization method of cyclohexane dicarboxylic acid of claim 1, wherein the oxide of the transition metal of Group 4 is monoclinic zirconia.

4. The isomerization method of cyclohexane dicarboxylic acid of claim 1, wherein the oxide of the transition metal of Group 4 is anatase titania.

5. The isomerization method of cyclohexane dicarboxylic acid of claim 1, wherein the isomerization catalyst is added in an amount such that the weight ratio of the isomerization catalyst to cyclohexane dicarboxylic acid is 0.1 to 2.0.

6. The isomerization method of cyclohexane dicarboxylic acid of claim 1, wherein the cyclohexane dicarboxylic acid is comprised in an amount of 0.8% by weight to 20% by weight with respect to the total weight of the mixed solution.

7. The isomerization method of cyclohexane dicarboxylic acid of claim 1, wherein the heat treatment is performed at 220° C. to 280° C.

* * * * *